US008672960B2

(12) United States Patent
Briganti et al.

(10) Patent No.: US 8,672,960 B2
(45) Date of Patent: Mar. 18, 2014

(54) METHOD AND APPARATUS FOR ENDOSCOPIC LIGAMENT RELEASE

(75) Inventors: Richard Thomas Briganti, Philadelphia, PA (US); Alan B. Miller, Jamison, PA (US); Charles F. Leinberry, Jr., Chester Springs, PA (US)

(73) Assignee: SEG-Way Orthopaedics, Inc, Carlsbad, CA (US)

( * ) Notice: Subject to any disclaimer, the term of this patent is extended or adjusted under 35 U.S.C. 154(b) by 21 days.

(21) Appl. No.: 13/183,020

(22) Filed: Jul. 14, 2011

(65) Prior Publication Data
US 2012/0016397 A1 Jan. 19, 2012

Related U.S. Application Data

(60) Provisional application No. 61/364,128, filed on Jul. 14, 2010.

(51) Int. Cl.
*A61B 17/32* (2006.01)

(52) U.S. Cl.
USPC ...................................................... 606/170

(58) Field of Classification Search
USPC ......... 606/138, 148, 150, 166, 167, 170, 171,
606/190, 191; 600/183; 30/289, 294;
422/119, 26, 28, 292, 400; 116/216,
116/207, 217, 219; 374/106, 160;
206/459.1, 459.5
See application file for complete search history.

(56) References Cited

U.S. PATENT DOCUMENTS

| | | | | |
|---|---|---|---|---|
| 5,089,000 A * | 2/1992 | Agee et al. | .................... | 606/170 |
| 5,273,024 A * | 12/1993 | Menon et al. | .................. | 600/114 |
| 5,282,816 A * | 2/1994 | Miller et al. | .................. | 606/167 |
| 5,325,883 A * | 7/1994 | Orr | ................................. | 128/898 |
| 5,472,415 A * | 12/1995 | King et al. | ..................... | 606/102 |
| 5,522,897 A * | 6/1996 | King et al. | ..................... | 606/102 |
| 5,569,283 A * | 10/1996 | Green et al. | .................. | 606/170 |
| 5,779,364 A * | 7/1998 | Cannelongo et al. | ......... | 374/160 |
| 5,827,311 A * | 10/1998 | Berelsman et al. | ........... | 606/167 |
| 6,019,774 A * | 2/2000 | Weiss et al. | .................... | 606/167 |
| 6,179,852 B1 * | 1/2001 | Strickland et al. | ............ | 606/167 |
| 7,141,214 B2 * | 11/2006 | Puntambekar | ................ | 422/119 |

(Continued)

OTHER PUBLICATIONS http://www.thefreedictionary.com/intact, dictionary definition of the term "intact".*

(Continued)

*Primary Examiner* — Ryan Severson
*Assistant Examiner* — David Eastwood
(74) *Attorney, Agent, or Firm* — Donn K. Harms

(57) ABSTRACT

The invention pertains to a method, apparatus, and system for cutting anatomic members, such as ligaments, in surgical procedures such as carpal tunnel release, plantar fasciotomy, gastroc release, cubital tunnel release, and tarsal tunnel release. The apparatus includes a retrograde knife and a guide tool for guiding the knife and a scope during surgery. Relevant features include a knife stop for preventing the knife from inadvertently raising out of the knife channel, indicators showing the proper orientation for the guide tool, a self dilating tip and channel design on the guide tool, a cover piece and/or pivotable panel system for preventing ligaments and other anatomy from getting caught in the guide tool, a pivot pin and groove system for stabilizing the knife and also assuring that the knife blade is not inadvertently raised out of the channel, and a use indicator for preventing re-use of a single use device.

6 Claims, 10 Drawing Sheets

(56) References Cited

U.S. PATENT DOCUMENTS

| | | | |
|---|---|---|---|
| 8,382,804 B2 * | 2/2013 | Thomke et al. | 606/267 |
| 2004/0054378 A1 * | 3/2004 | Yang | 606/191 |
| 2007/0215001 A1 * | 9/2007 | Voegele | 106/31.01 |
| 2009/0048620 A1 * | 2/2009 | Weiss et al. | 606/167 |
| 2009/0270856 A1 * | 10/2009 | Saadat et al. | 606/33 |
| 2011/0087255 A1 * | 4/2011 | McCormack et al. | 606/167 |
| 2011/0252651 A1 * | 10/2011 | Sewell | 30/289 |

OTHER PUBLICATIONS http://www.thefreedictionary.com/medallion, dictionary definition of the term "medallion".*

* cited by examiner

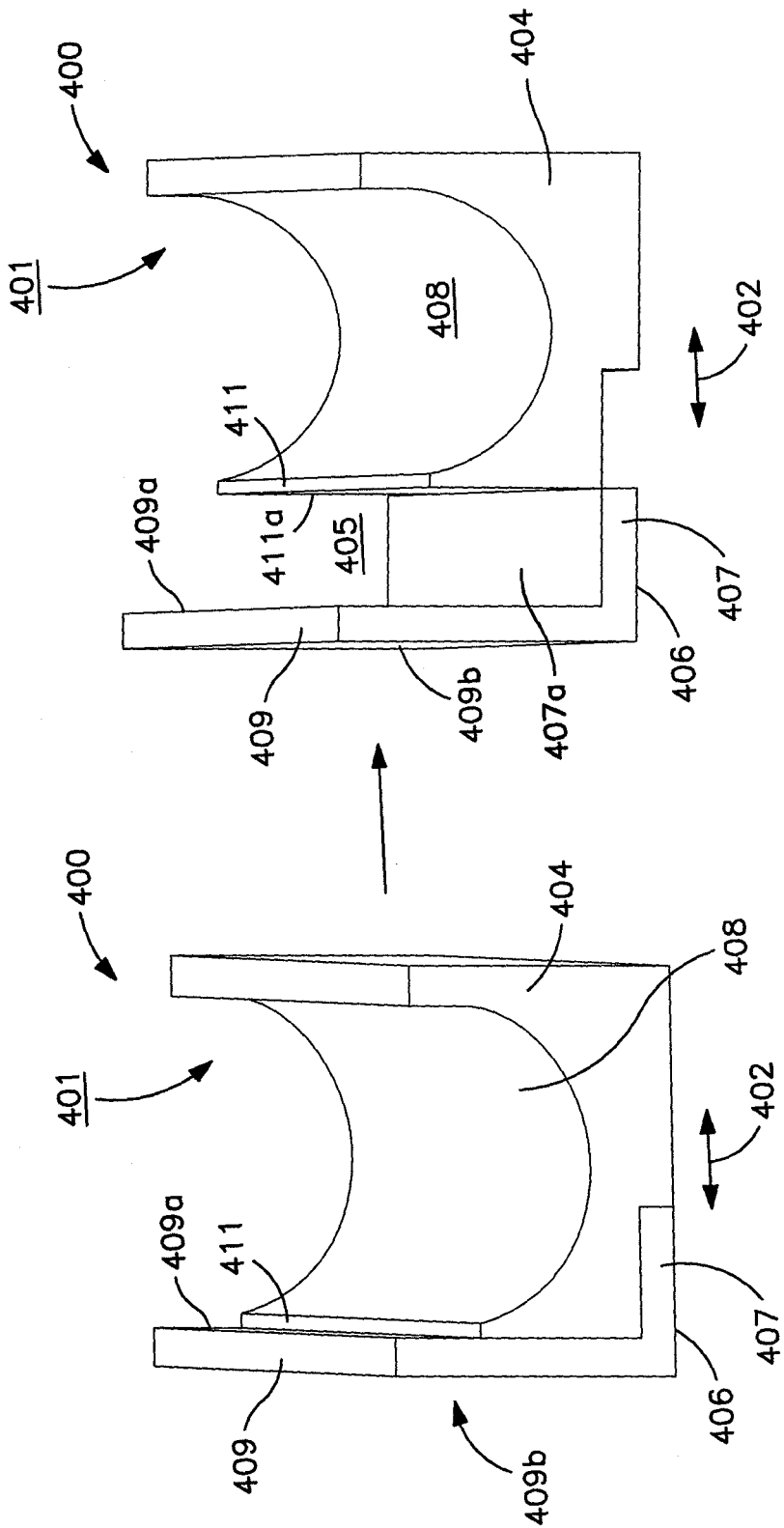

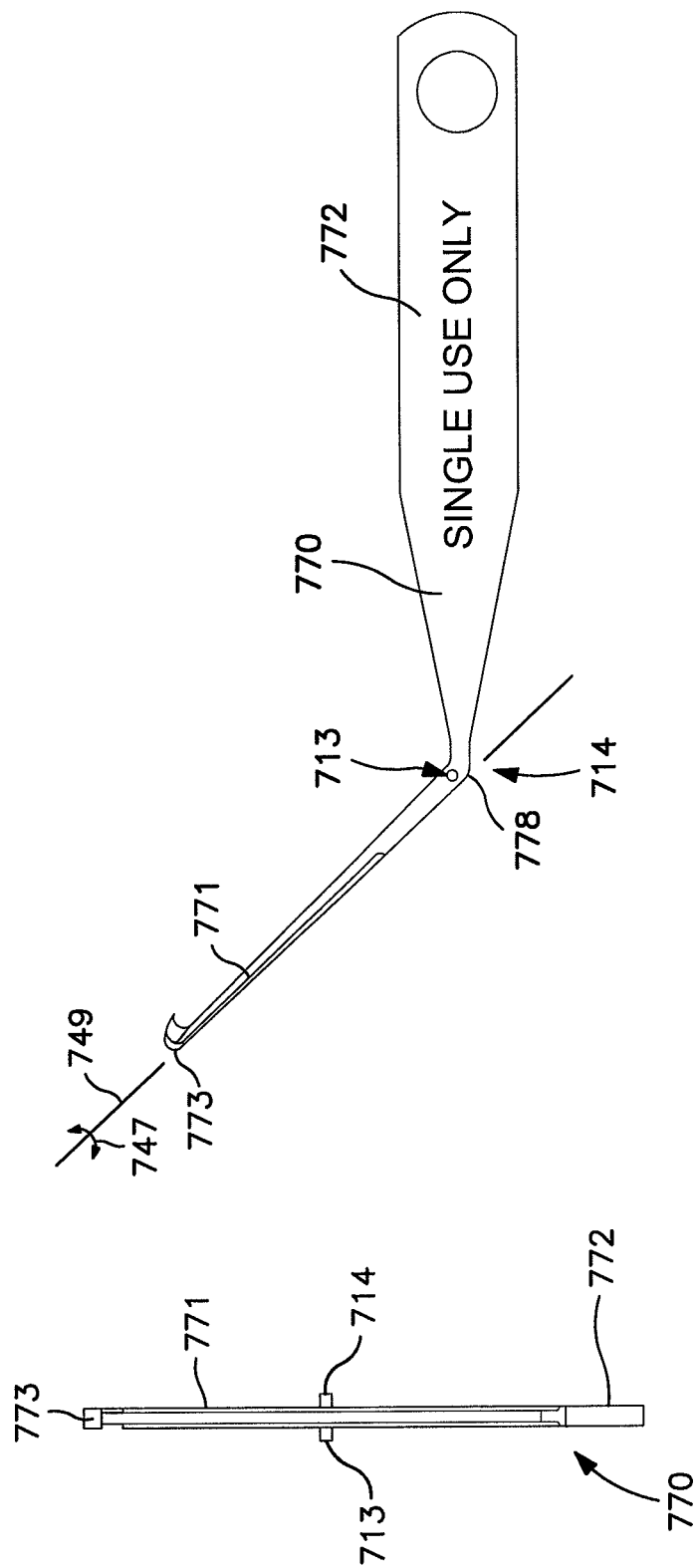

METHOD AND APPARATUS FOR ENDOSCOPIC LIGAMENT RELEASE

CROSS REFERENCE TO RELATED APPLICATIONS

This application claims the benefit of U.S. provisional application No. 61/364,128 filed on Jul. 14, 2010, which is fully incorporated herein by reference.

FIELD OF INVENTION

The invention pertains to methods, apparatus, and systems for performing endoscopic ligament release surgery, such as carpal tunnel release, plantar fasciotomy, gastroc release, cubital tunnel release, and tarsal tunnel release surgery, and similar surgical procedures on anatomic members.

BACKGROUND

Carpal tunnel syndrome occurs when the median nerve is squeezed where it passes through the carpal tunnel, thereby causing insanguination of the nerve, which leads to numbness, a cold feeling, and/or pain in the hand and fingers. The carpal tunnel is an anatomic passageway at the base of the wrist through which the median nerve and the flexor tendons for the fingers of the hand pass. It is defined by the carpal bones of the hand and the transverse carpal ligament. Carpal tunnel syndrome is commonly caused by highly repetitive hand motions over a number of years. For instance, carpal tunnel syndrome is common in certain professionals such as secretaries and other professionals who type on a keyboard regularly, carpenters, dentists or anyone who performs the same hand motions repeatedly and regularly.

The current standard of care for alleviating carpal tunnel syndrome is to incise the transverse carpal ligament to open up the carpal tunnel and release the pressure on the median nerve. With few exceptions, most people can manage daily activities with a severed transverse carpal ligament with almost no adverse effects.

The particular current procedure for carpal tunnel release is an endoscopic or arthroscopic procedure in which an incision is made in the wrist proximal of the carpal tunnel. An endoscope with a camera is inserted into the incision and through the carpal tunnel to allow the surgeon to visualize the carpal tunnel, and, particularly, the transverse carpal ligament, and then a knife is inserted alongside the endoscope to cut the transverse carpal ligament.

Referring to FIG. 1, one system available on the market today is the SEG-Way system offered by Core Essence Orthopedics, Inc. of Fort Washington, Pa., USA. The SEG-Way system comprises, among other things, a guide 10 and a retrograde knife 12. As seen in FIG. 1, the guide 10 compromises a longitudinal member 14, containing a channel 16. The channel 16 is for receiving the endoscope 20 and the knife 12 side-by-side. A key feature of the SEG-Way system is that the endoscope and knife are entirely independently manipulable. The guide further comprises a transverse member 19 at its proximal end comprising two wings 21 and 22 extending in opposition transverse directions from the proximal end 23 of the longitudinal member 14. The wings 21, 22 provide a place for the surgeon to hold the guide as well as some stability against rotation about the longitudinal axis 24 of the longitudinal member because the wings essentially rest upon the forearm 26 of the person after the guide has been inserted through the incision 25.

In use, the incision 25 is made in the wrist proximal to the carpal tunnel 27 and the longitudinal member 14 of the guide 10 is advanced distally into and through the carpal tunnel, thereby dilating the carpal tunnel. Once the guide 10 is fully inserted and through the carpal tunnel 27, the endoscope 20 is advanced through the first channel 16 to allow the surgeon to see the carpal tunnel, and particularly, the transverse carpal ligament 30. Then, the knife 12 is advanced distally within the channel 16. As can be seen in FIG. 1, the knife comprises a handle 34 and a distal segment 36 disposed at an angle 38 to each other and has a hooked, retrograde blade 29 at the distal end of the distal segment 36 that faces proximally and cuts when the knife is pulled back in the proximal direction. The angled junction 38 between the handle 34 and the distal segment 36 of the knife 12 generally defines a pivot point about which the knife will be rotated after insertion and prior to cutting. More particularly, the knife 12 is inserted into the channel 16 with the distal segment 36 lying flat in the channel 16 and flush against the bottom of the channel with the blade 29 concealed inside the channel 16 until it is past the transverse carpal ligament so as not to contact any anatomy. This inherently means that the handle segment 34 will be angled upwardly. Then, the surgeon pushes down on the handle to cause the distal segment, and particularly, the retrograde blade to rise up out of the channel 16 so that it can engage the distal edge 30a of the transverse carpal ligament 30 and cut it by drawing the knife 12 back in the proximal direction.

SUMMARY OF INVENTION

The invention pertains to a method, apparatus, and system for cutting anatomic members, such as ligaments, in surgical procedures such as carpal tunnel release, plantar fasciotomy, gastroc release, cubital tunnel release, and tarsal tunnel release. The apparatus includes a retrograde knife and a guide tool for guiding the knife and a scope during surgery. Relevant features include a knife stop for preventing the knife from inadvertently raising out of the knife channel, indicators showing the proper orientation for the guide tool, a self dilating tip and channel design on the guide tool, a cover piece and/or pivotable panel system for preventing ligaments and other anatomy from getting caught in the guide tool, a pivot pin and groove system for stabilizing the knife and also assuring that the knife blade is not inadvertently raised out of the channel, and a use indicator for preventing re-use of a single use device.

BRIEF DESCRIPTION OF THE DRAWINGS

FIG. 6A is a perspective view of a guide in a first condition in accordance with a fourth embodiment of the invention.

FIG. 6B is a perspective view of the guide of the fourth embodiment in a second condition.

FIG. 9B is a side view of a knife in accordance with the seventh embodiment of the invention FIG. 9C is a top view of the guide and knife of FIGS. 10A and 10B assembled.

DETAILED DESCRIPTION OF THE EMBODIMENTS

Figure 3:
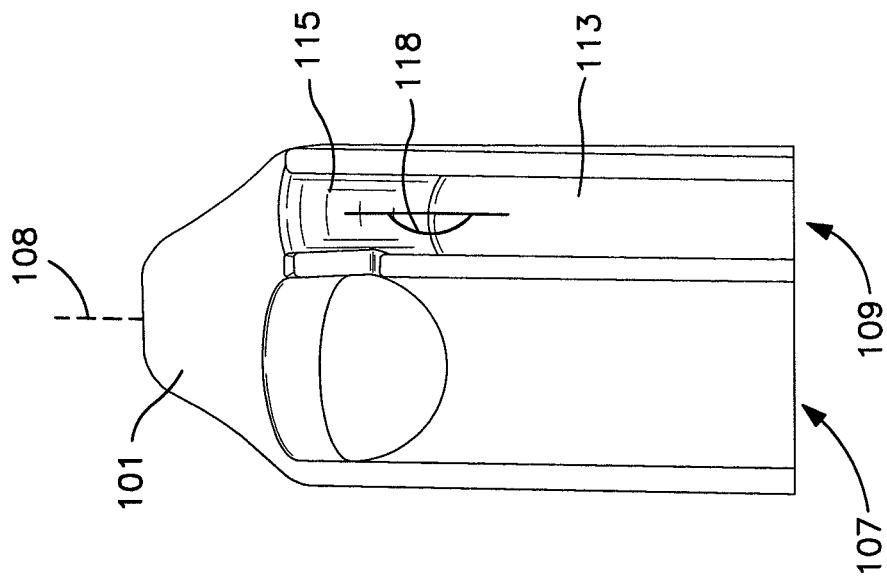
FIG. 3 is a close up view of the distal end of the guide of FIG. 2.
Figure 2:
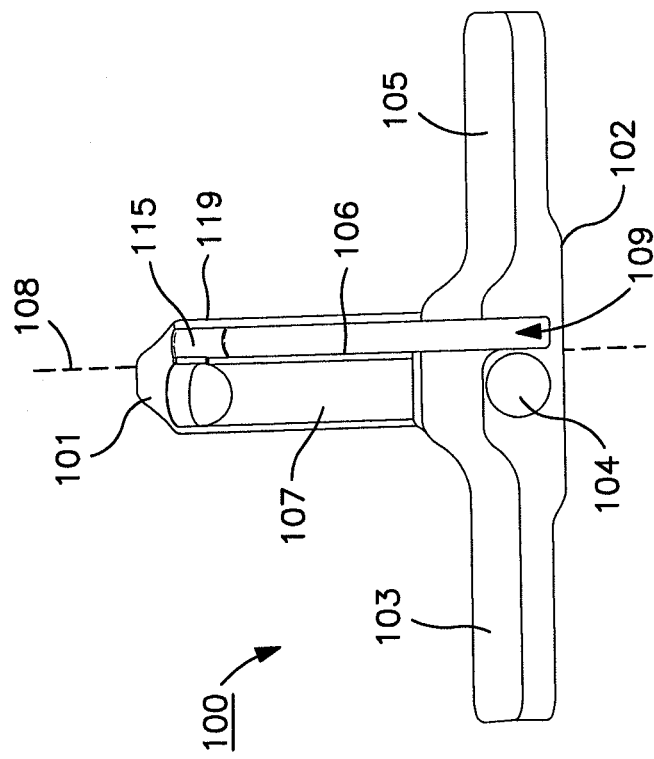
FIG. 2 is a perspective view of a guide in accordance with one particular embodiment of the invention.

FIG. 2 is a perspective view looking substantially from the proximal end of a guide member in accordance with a first embodiment of the present invention. FIG. 3 is a close up view of the distal end of the guide member of FIG. 2. The guide 100 comprises a longitudinal member 101 and a transverse member 102. The transverse member comprising two wings 103 and 105 extended laterally from the proximal end 104 of the longitudinal member 101. The longitudinal member 101 defines two channels 107 and 109 separated by a partition, such as a ridge 106 in a surface of the longitudinal member for accepting a scope, such as an endoscope or arthroscope, and a knife, respectively.

Figure 1:
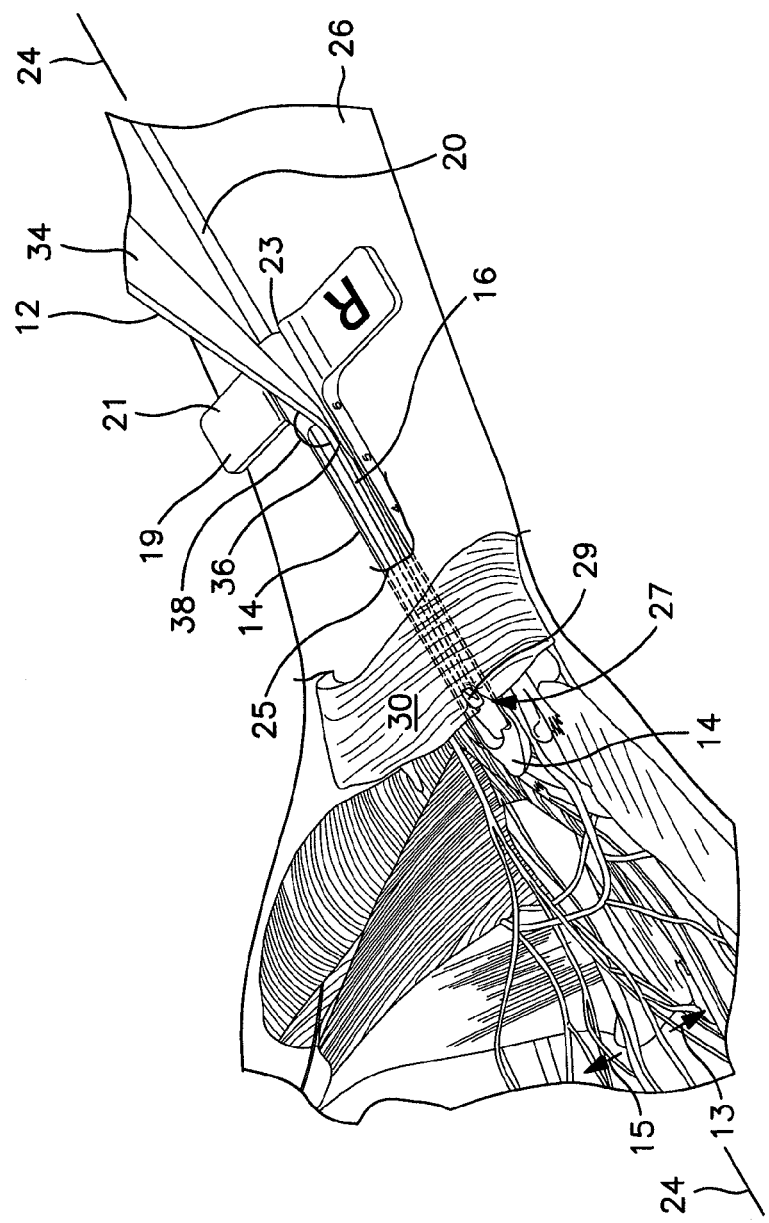
FIG. 1 is a diagram illustrating use of one particular endoscopic carpal tunnel release apparatus and method in accordance with the prior art.

One issue of which surgeons must be aware when using carpal tunnel release surgical systems of the type shown in FIGS. 1 and 2 is the fact that the cutting tip of the knife should remain concealed within the knife channel 109 so as not to accidentally engage anatomy when the knife is being inserted distally through the carpal tunnel. This, of course, is achieved by holding the knife handle at an angle to the longitudinal axis 108 so that the distal segment of the knife lays flat on the bottom surface 113 of the channel 109 as described above in connection with FIG. 1. However, if the knife is advanced distally far enough into the channel to engage the distal wall 115 of the channel 109, if that wall is at an obtuse angle to the longitudinal axis 108 of the guide, the wall may divert some of the distally directed advancing force on the knife upwardly, thereby deflecting the distal end of the knife, i.e., the blade to exit the safe area inside the channel 109 and possibly cut anatomy inadvertently.

Thus, in accordance with this embodiment of the invention, the end wall 115 of the channel 109 forms an angle 118 with the bottom 113 of the channel 109 that is substantial enough that any distally-directed advancing force on the knife is not easily redirected upwardly so as to cause the distal end of the knife to rise up out of the channel 109. This angle 118 may be a right angle (90°). However, it can be an acute angle so that engagement of the end of the knife with the wall 115 actually applies a downward force on the distal end of the knife. Generally, no downward motion of the distal end of the knife will actually occur because the distal segment of the knife already should be flush against the bottom 113 of the channel 109. However, if the surgeon is holding the knife at an incorrect angle so that the distal end of the knife is not flush against the bottom of the channel, the engagement with the end wall 115 may actually help by pushing the distal end of the knife down into the channel until it is flush with the bottom surface 113.

In other embodiments, the angle may even be slightly greater than 90°. Specifically, since there will be some friction between the knife and the wall 115 such that contact between the end of the knife and the wall under reasonably expected loads still would not result in the knife sliding upward along the end wall 115 and rising out of the channel.

Additionally, the ridge 106 between the endoscope channel 107 and the knife channel 109 helps prevent the endoscope and knife from inadvertently interfering with each other. Specifically, in prior devices having a single channel for containing both the endoscope and the knife, the scope and knife would often cross over into each other's spaces within the single channel, sometimes causing difficulty in individually advancing, withdrawing, tilting, turning, or otherwise moving the endoscope and/or knife. The present design with two channels 107, 109 separated by a ridge 106 essentially keep each of the endoscope and knife from crossing over into the channel of the other instrument and interfering with it.

Figure 4A:
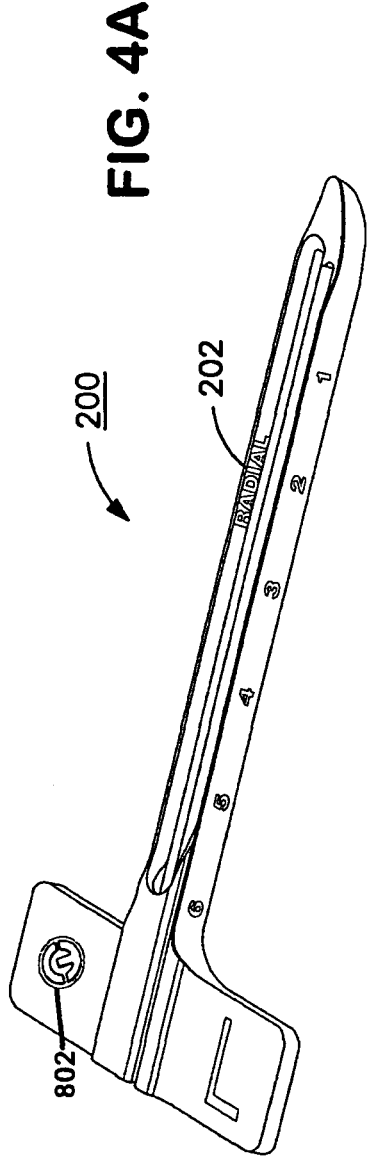
FIG. 4A is a perspective view of a guide in accordance with a second embodiment of the invention viewed from a first perspective.
Figure 4B:
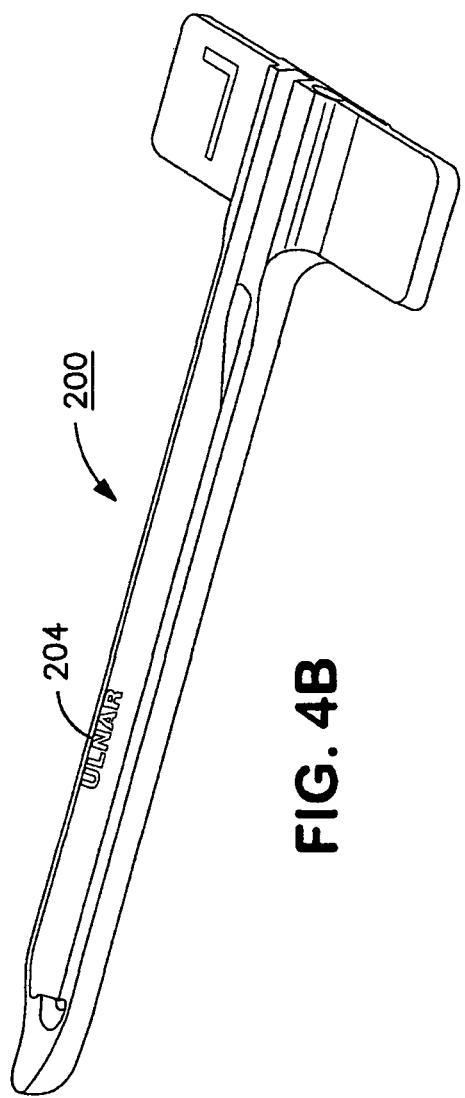
FIG. 4B is a perspective view the guide in accordance with the second embodiment of the invention viewed from a second perspective.

FIGS. 4A and 4B are right-side and left-side perspective views of a second embodiment of the guide 200 illustrating another feature. Particularly, with respect to the human body, medical personnel generally adhere to certain semantic conventions for clarity. For instance, the term "medial" is generally used to describe a direction towards the center of the body, and the term "lateral" is generally used to describe a direction away from the center of the body. However, with respect to the hands, this language is not sufficiently definite because a person can hold one's hand in different orientations, e.g., with the palm facing towards the sky or with the palm facing towards the ground. Accordingly, the terms medial and lateral are indefinite with respect to hands. Hence, with respect to the hand, the terms "ulnar" and "radial" often are used instead. Ulnar refers to the direction from the center of the hand towards the ulnar nerve. The ulnar nerve runs along the length of the hand on the pinky side of the hand. Accordingly, the ulnar direction is the direction transverse the length of the hand facing from the center of the hand towards the pinky as illustrated by arrow 13 in FIG. 1. Radial, of course, is the opposite direction, as illustrated by arrow 15 in FIG. 1.

When performing endoscopic carpal tunnel release surgery using a guide such as any of guides 10, 100, and 200, it is desirable to have the camera on the radial side and the knife on the ulnar side because the guide is inserted to the ulnar side of the medial nerve. This places the endoscope against the medial nerve, which is preferred because it separates the medial nerve from the knife for extra safety in avoiding accidental nicking of the medial nerve with the knife. Accordingly, it is desirable to provide different guides for the right hand and the left hand. Therefore, to help avoid confusion, the two guides should be clearly marked, such as with an L and an R for the left-hand and right-hand guides, respectively. FIGS. 4A and 4B, for instance, illustrate the left hand guide and, it can be seen that there is a prominent L printed on one of the transverse wings. Nevertheless, there still tends to be confusion during surgery as to the proper choice and orientation of the guide. Accordingly, in addition to clearly marking the guide as left or right, each guide member is also marked to indicate which side of the guide 200 should be facing towards the radial direction and the ulnar direction. This may be accomplished, for instance, by printing the words "radial" 202 and/or "ulnar" 204 on the sidewall of the channels as shown in FIGS. 4A and 4B.

Figure 5:
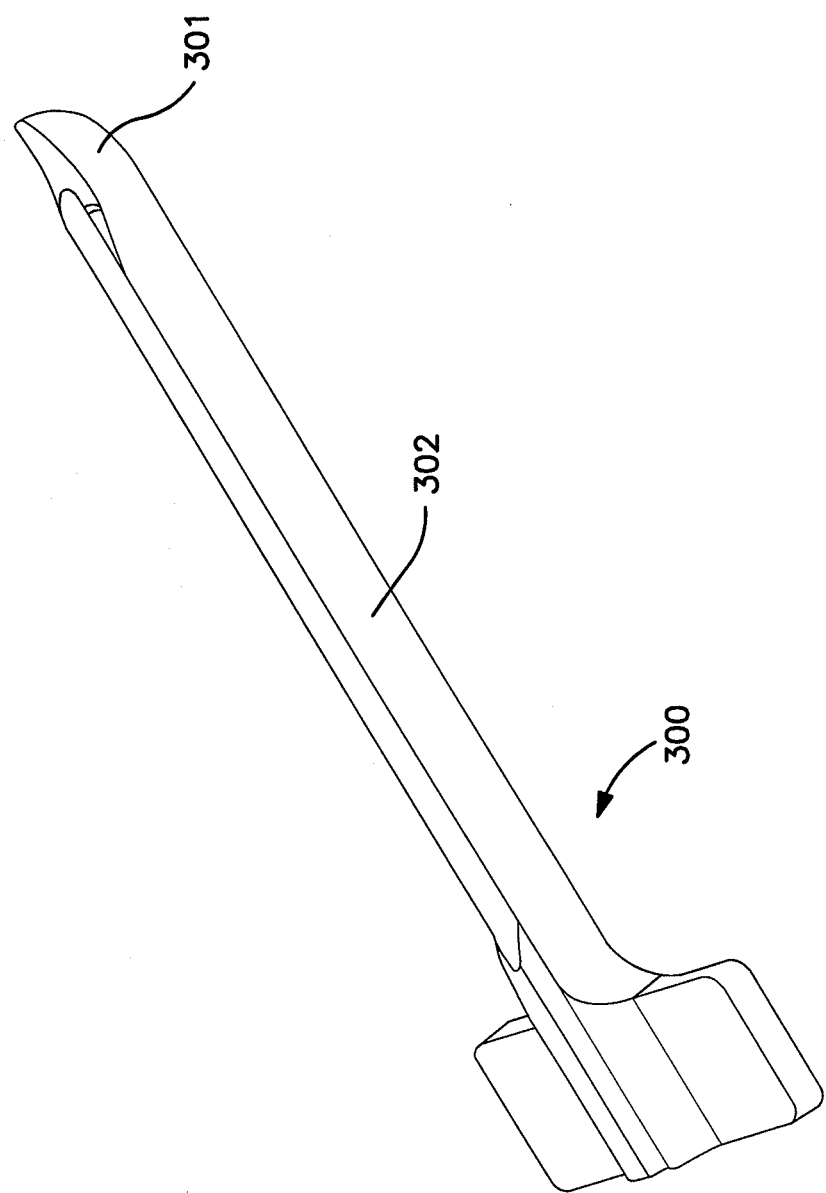
FIG. 5 is a perspective view of the distal portion of a guide in accordance with a third embodiment of the invention.

FIG. 5 is a perspective view of the distal end of a guide 300 according to a third embodiment. Particularly, as previously described, the distal tip of the guide leads the guide into and through the carpal tunnel. The carpal tunnel is rather tightly packed with flexor tendons and the median nerve. Accordingly, tip 301 is shaped to better assist in dilating the carpal tunnel and spreading the various flexor tendons and radial nerve to create room for the guide to pass through the carpal tunnel.

More specifically, the distal tip 301 of the guide 300 is prow shaped in order to ease the insertion of the distal tip of the guide into the carpal tunnel and to assist in the dilation of the carpal tunnel and the spreading of the flexor tendons and the medial nerve to allow the longitudinal member 302 of the guide to pass through the carpal tunnel. As can be seen, the distal tip is shaped like the prow of a boat. Particularly, it is pointy without being sharp and it is curved upward slightly.

FIGS. 6A and 6B illustrate an alternative embodiment of the longitudinal portion 401 of a guide 400 designed to even further ease insertion of the longitudinal portion 401 of the guide into the carpal tunnel and to more efficiently dilate the tunnel. In accordance with this embodiment, the longitudinal portion 401 of the guide 400 actually comprises two longitudinal members 404, 406 that are collapsible and expandable in the transverse dimension 402 relative to each other. In this manner, the longitudinal portion 401 of the guide 400 can be initially inserted into and through the carpal tunnel while in the collapsed condition shown in FIG. 6A in order to ease insertion by virtue of having a smaller profile in the transverse dimension (the ulnar/medial direction) and be expandable to the expanded condition shown in FIG. 6B to further dilate the carpal tunnel and provide the necessary room for the endoscope and knife within the longitudinal portion 401. In the exemplary embodiment illustrated in FIGS. 6A and 6B, the first longitudinal member 404 defines the endoscope channel 408 and the second longitudinal member 406 defines the knife channel 405. The second longitudinal member 406 is a transversely translatable L-shaped member. In the closed position, the bottom leg 407 of the L-shaped second longitudinal member 406 slides into a groove (not shown) under the endoscope channel 408 of the first longitudinal member 404 so that the vertical leg 409 of the L-shaped second longitudinal member 406 butts up against the ulnar-side wall 411 of the endoscope channel 408. This essentially collapses the knife channel 405 to nothing and reduces the cross-section of the guide portion 404. The longitudinal portion 404 of the guide 400 can be initially inserted into and through the carpal tunnel in the collapsed condition shown in FIG. 6A. Then, after initial insertion and, perhaps, after waiting a designated period of time to allow the carpal tunnel to dilate and adjust to accommodate the collapsed longitudinal portion 401, the L-shaped second longitudinal member 406 can then be slid transversely outwardly into the expanded condition illustrated in FIG. 6B, with the bottom leg 407 of the L-shaped member 406 sliding out from under the first longitudinal member 404 to open the knife channel 405.

The mechanism for permitting the longitudinal member to be collapsible and expandable may take many forms. One such mechanism comprises transverse grooves in the bottom leg 407 of the L-shaped member 406 that mate with pegs protruding from underneath the endoscope channel 408. The transverse grooves can slide laterally relative to the pegs. The transverse grooves may have detents at two positions to provide a higher resistance to transverse sliding when in the fully collapsed position and the fully opened position. The movement between the collapsed position and open position can be actuated by any number of mechanisms. For instance, a turnbuckle-type screw runs through a longitudinal channel underneath the endoscope channel 408, the proximal half of the screw being right-hand threaded and the distal half of the screw being left-hand threaded. Each half of the screw bears a matingly threaded wedge-shaped nut that sits within a mating cut out in the bottom leg 407 of the L-shaped member 406. The proximal end of the screw protrudes from the proximal end of the longitudinal member and has a thumb wheel to allow the surgeon to turn it by hand. Instead of a thumb wheel, the screw may have a contoured head that mates with an instrument, such as a screwdriver, to turn the screw. When the screw is turned in one direction, the mating threads in the wedges and on the screw cause the wedges 437, 438 to move toward each other; causing the edges of the wedges to travel along the adjacent edges of the cutouts, thus pushing the L-shaped member 406 transversely outward.

This exposes (or creates) the knife channel 405, which is defined by the inner surface 409a of upper leg 409 of the L-shaped second longitudinal member 406, the upper surface 407a of the bottom leg 407 of the L-shaped second longitudinal member 406, and the ulnar-side outer surface 411a of the first longitudinal member 404. The endoscope and knife can then be advanced into their respective channels 408 and 405 and the procedure performed. After the procedure is performed and the knife and endoscope are withdrawn from their channels, the screw may be turned in the opposition direction. The force of the wedge pushing the L-shaped second longitudinal member transversely outward is thus released and the surrounding forces of the flexor tendons, median nerve, and other anatomy in the carpal tunnel on the outer surface 409b of upper leg 405 of the L-shaped member 406 will push the L-shaped member 406 back to the collapsed position shown in FIG. 6A. The guide 400 may then be withdrawn while in this collapsed state. If desired, the edges of the wedge nuts can be provided with pegs that fit within further grooves in the adjacent edges of the triangular cutouts so that the pegs cannot escape from the grooves, but can only travel within the grooves. In this manner, turning the screw in the opposite direction will actually draw the L-shaped member back inwardly in and of itself without the need to rely on any external forces from the tendons and/or medial nerve in the carpal tunnel.

Figure 7B:
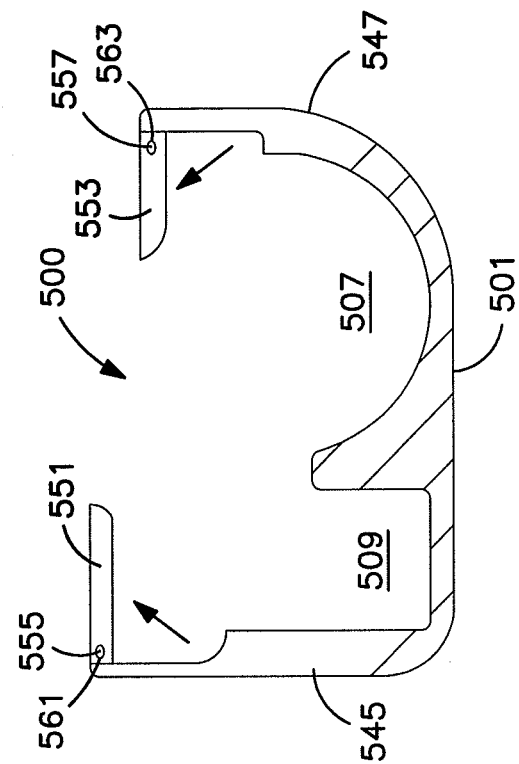
FIG. 7B is a cross sectional side view of a distal longitudinal member of a guide in a second condition in accordance with the fifth embodiment of the invention.
Figure 7A:
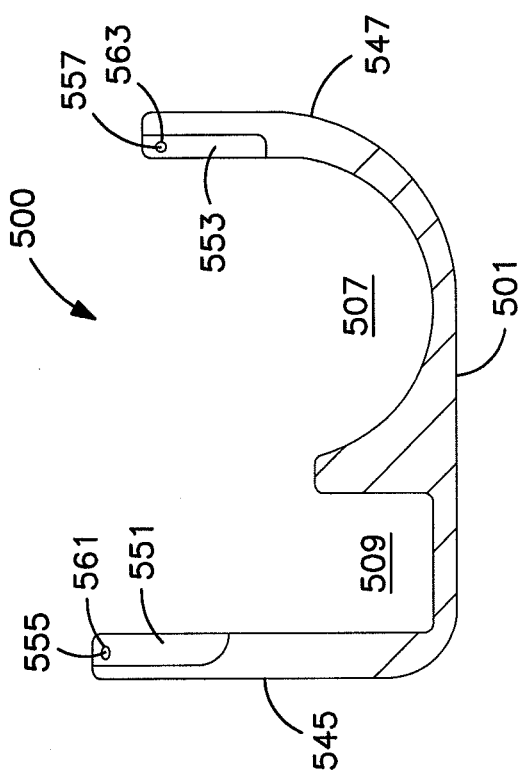
FIG. 7A is a cross sectional side view of the longitudinal member of a guide in a first condition in accordance with a fifth embodiment of the invention.

FIGS. 7A and 7B illustrate a fifth embodiment of a guide 500. Particularly, FIGS. 7A and 7B are transverse cross-sectional slices of the longitudinal member 501 of the guide 500 in accordance with this embodiment. FIG. 7A illustrates the closed position and FIG. 7B illustrates the open position. In this embodiment, the outer walls 545, 547 of the endoscope and knife channels 507, 509 bear panels 551, 553 that are rotatable on pins 555, 557 between a first position as illustrated in FIG. 7A and a second position as illustrated in FIG. 7B.

Initially and throughout most of the procedure, the panels remain in the first position and simply form part of the walls 545, 547 of the two channels 507, 509. However, after the ligament has been cut and the guide 500 is to be withdrawn from the carpal tunnel, the panels 551, 553 may be flipped into the closed position illustrated in FIG. 7B to help prevent pieces of the cut ligament or other anatomy from falling into the channels 507, 509.

Particularly, it is not uncommon for pieces of the cut ligament to hang down into the channels of the longitudinal member 501 of the guide 500 and potentially be pulled by the guide 500 as it is withdrawn, which would cause unnecessary pain and possible damage to the patient. In accordance with this embodiment, the panels 551, 553 can be rotated into the second position shown in FIG. 7B. As can be seen in FIG. 7B, in this position, the panels 551, 553 block off a significant portion of the channels 507, 509. As they are rotated up, the panels would tend to push out any ligament that has fallen into the channel. Furthermore, as the guide 500 is withdrawn from the carpal tunnel, the panels will substantially prevent ligament strands and other anatomy from falling into the channel and potentially getting caught in the channels.

In the illustrated embodiment, the panels 551, 553 do not fully close off the channels 507, 509. This is acceptable because the ligaments tend to get caught on the edges of the channels rather than in the middles of the channels. However, if desired, the panels 551, 553 can be made wide enough to meet each other in the second position to completely close off all of the channels. Preferably, the panels 551, 553 run the entire length of the channels, but shorter lengths that leave a small portion of the channels exposed at either the proximal or distal end of the channels would be acceptable.

The mechanism for rotating the panels between the first and second positions can take many forms. In the illustrated embodiment, the panels are fixedly mounted on longitudinal pins 555, 557 that run in holes 561, 563 the full length of the channels 507, 509. The proximal ends of those pins 555, 557 protrude from the proximal end of the longitudinal member and bear thumb wheels for allowing the surgeon to rotate the pins 555, 557. The panels 551, 553 can be fixable in any position, not just the first and second positions. For instance, at least the proximal ends of the pins can be threaded and nuts 565, 567 can be provided near the proximal end of each pin and so that the nuts can be rotated on the pins as desired to abut the proximal end of the longitudinal member 501 and thereby lock the pins/panels in any desired orientation.

The panels 551, 553 also may be rotated and locked in the second positions to close off the channels during initial insertion of the guide 500 into and through the carpal tunnel. Particularly, although less common, it is possible for the transverse carpal ligament, flexor tendons, medial nerve or other anatomy to get caught in one of the channels 507, 509 during insertion too. Accordingly, it may be desirable to flip up the panels during both insertion and withdrawal of the guide from the carpal tunnel or other anatomical passageway.

Figure 8B:
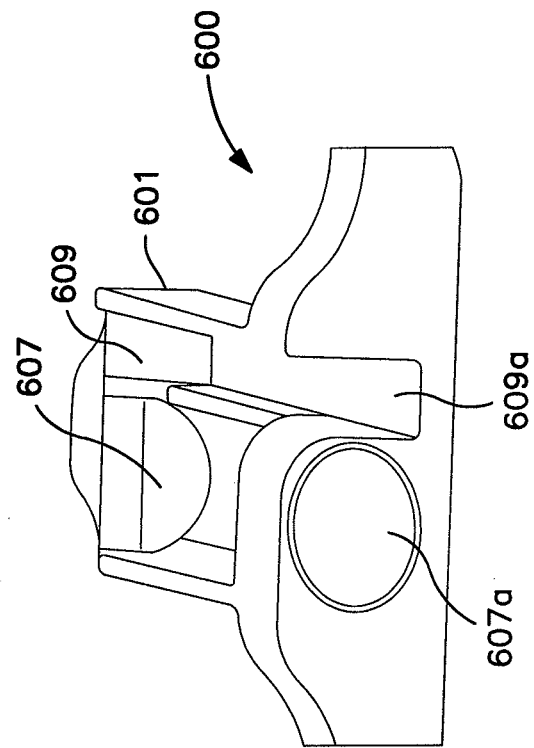
FIGS. 8A and 8B show a cover member and guide, respectively, in accordance with a sixth embodiment of the invention.
Figure 8A:
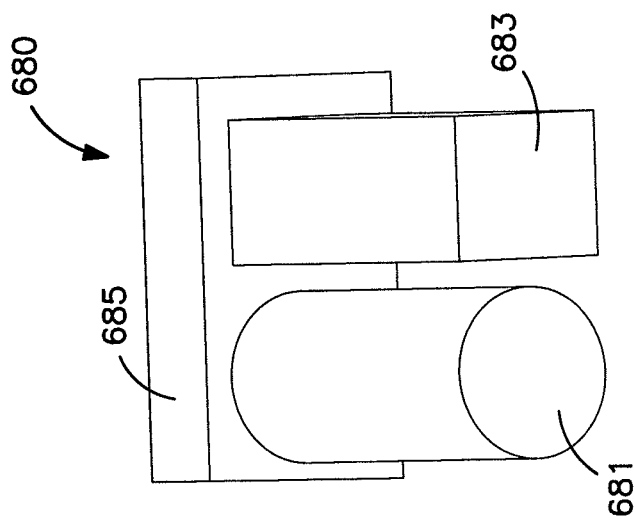

FIGS. 8A and 8B illustrate aspects of a sixth embodiment of the invention having some of the same advantages as the fifth embodiment described above in connection with FIGS. 7A and 7B.

More particularly, in this embodiment, a cover piece 680 illustrated in FIG. 8A is provided to completely cover the channels 607, 609 in the longitudinal member 601 of the guide 600 (illustrated in FIG. 8B) during insertion into and/or withdrawal. In this embodiment, the cover 607 piece comprises two members 681, 683, one shaped to exactly fill the endoscope channel 607 and the other shaped to exactly fill the knife channel 609. The two members 681, 683 are joined to each other through a proximal end piece 685. The cover piece is inserted simply by pushing it distally into the longitudinal member from the proximal end openings 607a, 609a of the channels 607, 609. The cover piece 680 fully fills both channels 607, 609.

In use, the cover piece 680 is inserted into the longitudinal member 601 prior to insertion of the guide 600 into the carpal tunnel. The cover piece 680 serves the purpose of closing off the channels, thereby preventing ligaments and other fibers from getting caught in the channels as the guide is advanced into and through the carpal tunnel. Once the guide 600 is inserted, the cover member 680 can be withdrawn proximally to expose the channels 607, 609 so that the endoscope and knife can be inserted into their respective channels. If desired, after the procedure is performed, the cover member 680 may be reinserted into the channels 607, 609 prior to withdrawing the guide 600 from the carpal tunnel in order to again close off the channels and prevent ligament strands and other fibers from getting caught in the channels as the guide is pulled out.

Figure 9A:
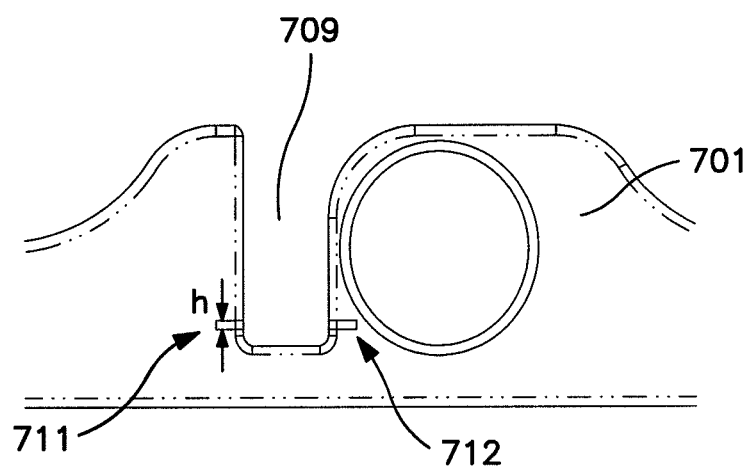
FIG. 9A is a transverse cross-section of a guide in accordance with a seventh embodiment of the invention.

FIGS. 9A, 9B, and 9C illustrate a seventh embodiment of the invention. FIG. 9A is a transverse cross-section view through the guide of this embodiment. FIG. 9B is a side view of the knife in accordance with the seventh embodiment. FIG. 9C is a top view of the knife in accordance with the seventh embodiment. In this embodiment, two pin grooves 711, 712 are provided in the knife channel 709 of the longitudinal member 701 of the guide 700, the pin grooves 711, 712 are open to the proximal end of the guide. Mating pins 713, 714 for sliding in the grooves 711, 712 are provided on the body of the retrograde knife 770. Hence, the height of the pin grooves 711, 712 within the knife channel 709 and the position of the pins 713, 714 on the knife 770 are selected so that, when the knife is inserted into the channel with the longitudinal dimension of the distal portion 771 of the knife 770 parallel to the channel 709 and concealed within the channel 709, the pins 713, 714 meet the grooves 711, 712 and can ride within the grooves in the longitudinal direction, thereby allowing the knife 770 to slide freely in the knife channel 709 in the longitudinal direction, but fixing the height of the knife in the channel at the location of the pins. The mating grooves 711, 712 and pins 713, 714 provide a defined position about which the knife can be pivoted to raise the retrograde blade out of the channel for cutting the ligament. More particularly, the height of the pivot point is fixed by the height of the grooves 711, 712. However, while the pivot pins 713, 714 define the precise axis about which the knife can be pivoted, the longitudinal position of those pins within the grooves is freely and fully adjustable within the grooves.

The combination of the pivot pins 713, 714 and the pivot grooves 711, 712 also provides increased stability to the knife 770 during distal advancement of the knife into the channel 709 insofar as the height of the knife is vertically fixed in the channel at the point where the pivot pins are positioned on the knife. As long as the surgeon maintains a neutral or upward force on the handle 772 of the knife, the distal segment 771 of the knife will remain entirely in the knife channel 709. On the other hand, in the absence of the pivot pins and grooves, the surgeon would need to be much more careful when inserting the knife to assure that the entire distal segment 771 of the knife 770 remained in the channel 709. Even further, the pivot pins/grooves combination also provides greater knife stability against roll (see arrow 747) about the longitudinal axis 749 of the distal segment 771 of the knife 770.

The pivot pins 713, 714 should be positioned on the knife 770 at an axis around which it is most desirable to pivot the knife. This will usually be at or very near the point 781 defining the base of the angle between the handle portion 772 of the knife and the distal portion 771 of the knife. The diameter of the pivot pins 713, 714 should be very close to the height, h, of the pivot pin grooves 711, 712 so that there is very little vertical play between the pivot pins and the pivot pin grooves, but should allow the pins to slide freely in the grooves. The grooves may run the entire length of the knife channel so that the knife can be advanced into the channel to any desired distance. However, in accordance with another embodiment, the groove may have a defined length, l, from the proximal end of the knife channel 709 so that the knife 770 cannot advance distally past the point where the pins 713, 714 on the knife hit the ends of the grooves 711, 712. This length, for instance, may be selected to prevent the distal end 773 of the knife from hitting the distal wall of the knife channel 709. This would be another potential mechanism for preventing the end of the knife from hitting the end wall of the channel and potentially being damaged and/or accidentally riding up the end wall 710 and out of the channel 709 inadvertently, as discussed above in connection with the embodiment of FIGS. 2 and 3.

Although the various features disclosed herein have been described in connection with different embodiments of a guide, it should be understood that any and all of the features of each embodiment may be combined in the same instrument in virtually any permutation.

Figure 10B:
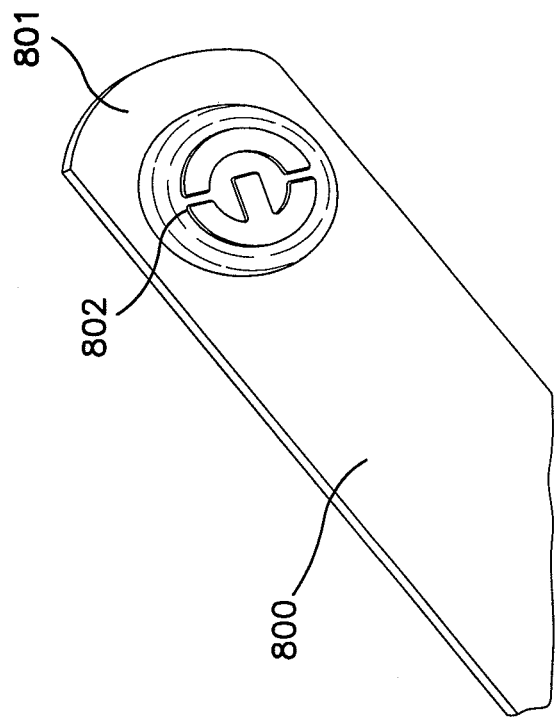
FIG. 10B is a close up perspective view of the proximal end of the knife in accordance with the eighth embodiment.
Figure 10A:
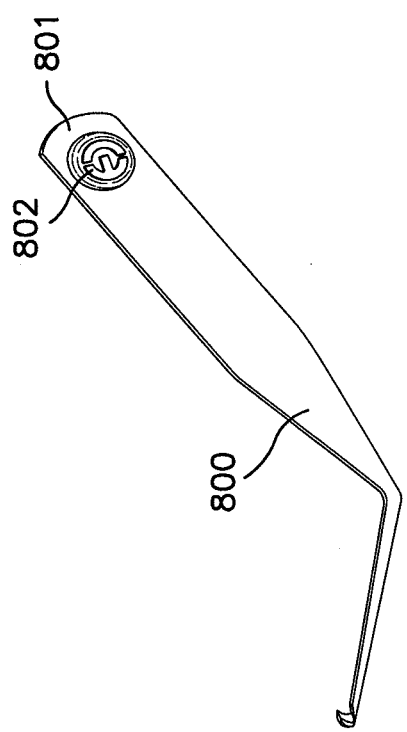
FIG. 10A is a perspective view of a knife prior to sterilization in accordance with an eighth embodiment of the invention.

In accordance with another aspect of the invention and with reference to FIGS. 10A and 10B, a portion 802 of the knife 800, preferably on the handle 801 is composed of a material different than the rest of the knife, which material cannot survive an autoclaving process intact. FIGS. 10A and 10B show the knife prior to sterilization. This is a desirable feature because it will provide an easily identifiable visual cue that the knife has been autoclaved. More particularly, in accordance with at least one embodiment, the entire system, including the guide, knife, and any other related instruments, such as a ligament rasp or a probe, are single-use surgical instruments, i.e., they can only be used once and then should be discarded. However, it is not uncommon for either medical staff or medical equipment resellers to inadvertently or even intentionally attempt to re-use or re-sell medical equipment that is intended only for a single use. In order to reuse any surgical instrument, it must be sterilized after the first use, which usually involves an autoclaving process. Accordingly, providing a portion 802 of the knife that is made of a material that cannot survive autoclaving, can provide a easy visual reference that the device has been previously used, and therefore should not be used again. In the embodiment illustrated in FIGS. 10A and 10B, the portion is a circular medallion 802 near the proximal end of the handle 801. The knife 800 generally will be made of a biocompatible metal, such as titanium or nitinol. The medallion, however, may be made of a polymer that will melt or otherwise degrade when subjected to a conventional autoclaving process (or any other process that might be used to re-sterilize a medical instrument).

In one embodiment, the medallion may run through the entire width, w, of the handle so that, after autoclaving, a hole will be left in the handle. However, in another embodiment, the button may only comprise a surface layer of material which, when destroyed reveals an underlying nondegradable material, such as the same material that the rest of the knife is made of, bearing a warning indicator indicating that the device has been used and should be not re-used, such as the words "Warning, this instrument has been used and should be discarded" or simply "Discard".

Having thus described a few particular embodiments of the invention, various alterations, modifications, and improvements will readily occur to those skilled in the art. Such alterations, modifications, and improvements as are made obvious by this disclosure are intended to be part of this description though not expressly stated herein, and are intended to be within the spirit and scope of the invention. Accordingly, the foregoing description is by way of example only, and not limiting. The invention is limited only as defined in the following claims and equivalents thereto.

The invention claimed is:

1. An apparatus for performing anatomical member release surgery comprising:
    a knife for cutting an anatomical member;
    a guide tool for guiding the knife;
    a medallion on at least one of the knife and the guide tool formed of a material that cannot survive a medical sterilization process intact; and
    a use indicator disposed on at least one of the knife and the guide tool, so as to be concealed from view by the medallion when the medallion is intact, and so as to be at least partially exposed to view, when the medallion is not intact.

2. The apparatus of claim 1 wherein the medallion is formed of a polymer.

3. The apparatus of claim 1 wherein the medallion cannot survive an autoclaving process intact.

4. A guide tool for performing anatomical member release surgery comprising:
    a longitudinal member having a proximal end, a distal end, a longitudinal axis, and a longitudinal surface extending between the proximal end and the distal end;
    a first longitudinal channel in the longitudinal surface of the longitudinal member for accepting a knife, the first longitudinal channel being open to the proximal end of the longitudinal member and having an end wall at the distal end of the longitudinal member;
    the first longitudinal channel having a bottom surface opposite the longitudinal surface of the longitudinal member, the bottom surface and the end wall forming an acute angle with each other; and
    a second longitudinal channel adapted to accept an endoscope, the first and second channels lying side-by side; and
    a longitudinally-directed partition between the first longitudinal channel and the second longitudinal channel.

5. The guide tool of claim 4 wherein the partition comprises a ridge.

6. The guide tool of claim 4 wherein the end wall adjacent the distal end of the longitudinal member acts as a stop for a knife advanced distally in the first longitudinal channel.

* * * * *